United States Patent [19]

Buckle et al.

[11] 4,263,299

[45] Apr. 21, 1981

[54] HETEROCYCLIC COUMARIN DERIVATIVES

[75] Inventors: Derek R. Buckle, Redhill; Harry Smith, Maplehurst, both of England

[73] Assignee: Beecham Group Limited, England

[21] Appl. No.: 85,038

[22] Filed: Oct. 15, 1979

[30] Foreign Application Priority Data

Oct. 20, 1978 [GB] United Kingdom .............. 41322/78
Jul. 4, 1979 [GB] United Kingdom .............. 23354/79

[51] Int. Cl.³ ........................................ C07D 405/02
[52] U.S. Cl. ................................. 424/250; 544/376
[58] Field of Search ........................ 544/376; 424/250

[56] References Cited

U.S. PATENT DOCUMENTS 4,092,416  5/1978  Winter et al. .................... 544/376

FOREIGN PATENT DOCUMENTS 2123924 11/1972  Fed. Rep. of Germany .
1335946 10/1973  United Kingdom .

Primary Examiner—Nicholas S. Rizzo
Attorney, Agent, or Firm—Jacobs & Jacobs

[57] ABSTRACT

A compound of formula (I):

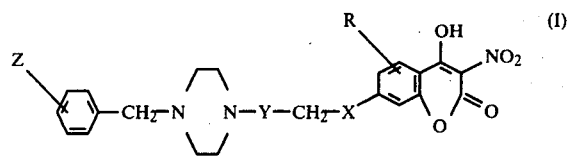

and pharmaceutically acceptable salts thereof, wherein R is hydrogen or an alkyl group containing up to 6 carbon atoms; X is a bond or oxygen; Y is —$(CH_2)_n$— where n is 0 or an integer from 1 to 5 wherein one carbon atom not bound to the nitrogen atom may be optionally substituted with a hydroxy group; and Z is hydrogen or halogen; may be used in the prophylaxis and treatment of diseases whose symptoms are controlled by the mediators of the allergic response, for example asthma, hay-fever, rhinitis and allergic eczema.

24 Claims, No Drawings.

HETEROCYCLIC COUMARIN DERIVATIVES

This invention relates to certain novel 3-nitrocoumarin derivatives, to a method for their preparation, to pharmaceutical compositions comprising such compounds and to their use in the treatment of certain allergic conditions.

It is known that some types of cells are activated by certain antibody-antigen combinations and release substances which mediate the allergic response. British Patent Specification No. 1454247 discloses that certain substituted 3-nitrocoumarins have useful activity in that they appear to inhibit the release of substances such as histamine which are normally released after antibody-antigen combinations and which mediate the allergic response.

We have now discovered a class of compounds which not only inhibit the release of mediator substances but also antagonize the effects of histamine released after the above mentioned antibody-antigen combinations. Thus these compounds are of value in the prophylaxis and treatment of diseases whose symptoms are controlled by the mediators of the allergic response, for example asthma, hay-fever, rhinitis and allergic eczema.

Accordingly, this invention provides a compound of the formula (I):

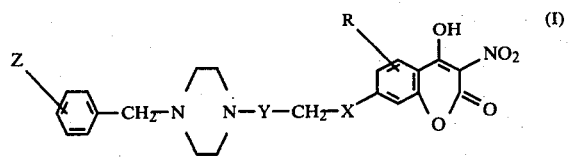

and pharmaceutically acceptable salts thereof, wherein R is hydrogen or an alkyl group containing up to 6 carbon atoms; X is a bond or oxygen; Y is —(CH$_2$)$_n$— where n is O or an integer from 1 to 5 wherein one carbon atom not bound to the nitrogen atom may be optionally substituted with a hydroxy group; and Z is hydrogen or halogen.

R may suitably represent hydrogen or an alkyl group such as methyl, ethyl or n-propyl. R may occupy any one of positions 5, 6 or 8 of the coumarin nucleus in compounds of formula (I) but most suitably occupies position 8.

X is usefully oxygen.

By way of example Y may represent alkylenes and hydroxyalkylenes such as methylene, ethylene, propylene, or butylene, hydroxyethylene or hydroxypropylene. Preferably Y is an alkylene such as methylene, ethylene or propylene, most preferably ethylene. Where Y is an hydroxyalkylene the compound (I) is asymmetric, and it is to be understood that when in this specification reference is made to compounds of formula (I) this reference includes pure enantiomers as well as racemic mixtures.

By way of example, Z may represent hydrogen, chlorine or bromine, but is preferably chlorine. While as indicated Z when halogen can substitute its phenyl ring at the o, m- or p-positions, it preferably substitutes at the p-position.

From the aforesaid it will be appreciated that one particularly useful sub-group of compounds within formula (I) is of formula (I)':

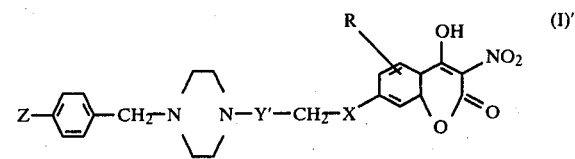

and pharmaceutically acceptable salts thereof, wherein R is hydrogen or an alkyl group containing up to 6 carbon atoms; X is a bond or oxygen; Y' is —(CH$_2$)$_n$— where n is O or an integer from 1 to 5; and Z is hydrogen or halogen.

In formula (I)' suitable and preferred examples of R include those described for R in formula (I).

In formula (I)' X is usefully oxygen.

In formula (I)' suitable and preferred examples of Y' include those described for non-hydroxy substituted Y groups in formula (I).

Z in formula (I)' is suitably hydrogen, chlorine or bromine, preferably chlorine.

Examples of particular compounds falling within formula (I) are:

1-(4-chlorobenzyl)-4-[3-(4-hydroxy-3-nitrocoumarin-7-yloxy)propyl]piperazine, 1-(4-chlorobenzyl)-4-[2-hydroxy-3-(4-hydroxy-3-nitrocoumarin-7-yloxy)propyl]piperazine, 1-(4-chlorobenzyl)-4-[2-hydroxy-3-(4-hydroxy-3-nitro-8-n-propylcoumarin-7-yloxy)propyl]piperazine, 1-(4-chlorobenzyl)-4-[(4-hydroxy-3-nitrocoumarin-7-yl)methyl]piperazine, 1-(4-chlorobenzyl)-4-[2-(4-hydroxy-3-nitrocoumarin-7-yloxy)ethyl]piperazine and 1-benzyl-4-[3-(4-hydroxy-3-nitrocoumarin-7-yloxy)propyl]piperazine.

Compounds of the formula (I) contain an acidic hydroxyl moiety at position 4 of the coumarin nucleus and may therefore form salts with pharmaceutically acceptable bases and salt forming cations. Compounds of the formula (I) also contain a piperazino moiety and may therefore form acid addition salts.

Examples of salts of the acidic hydroxyl moiety include metal salts, for example aluminium, alkali metal salts such as sodium or potassium, alkaline earth metal salts such as calcium or magnesium, and ammonium or substituted ammonium salts for example those with lower alkylamines such as triethylamine; cycloalkylamines such as dicyclohexylamine; or more complex amines and amino acids, e.g. N-ethylpiperidine, N-methylglucamine, alanine and serine.

Suitable acid addition salts of the compounds of the formula (I) include, for example inorganic salts such as the sulphate, nitrate, phosphate, and borate; hydrohalides e.g. hydrochloride, hydrobromide, and hydroiodide; and organic acid addition salts such as acetate, tartrate, maleate, citrate, succinate, benzoate, ascorbate, methanesulphonate, p-toluenesulphonate and trifluoroacetate.

This invention also provides a process for the preparation of compounds of formula (I), which process comprises reacting a compound of formula (II) or a salt thereof:

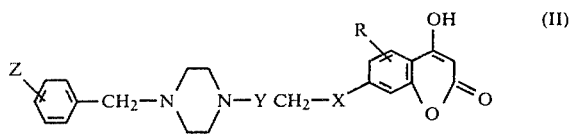

wherein R, X, Y and Z are as defined with respect to formula (I) with a nitrating agent.

Nitration may be effected by any conventional nitrating agent for example:

(i) acetic acid and concentrated nitric acid (ii) fuming nitric acid in chloroform The temperature at which the reaction is performed is dependant upon the nitrating reagent employed. Preferably the nitrating agent is fuming nitric acid in chloroform and the reaction is performed at a temperature range from $-5°$ to $+30°$ C., most preferably at about $10°$ to $15°$ C., for between 60 and 100 minutes.

The coumarins of formula (II) are novel useful intermediates and as such they form a further aspect of this invention.

Intermediates of formula (II) wherein X is oxygen may be prepared by reacting either of the protected coumarins (III) and (IV) respectively:

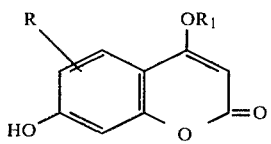

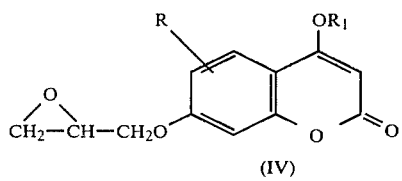

wherein $R_1$ is benzyl or $C_1$ to $C_6$ alkyl such as ethyl; using a suitable derivative of an appropriate piperazine. Such reactants are carried out by standard procedures. The resultant product may be deprotected by hydrogenation or acid hydrolysis as appropriate.

Where intermediates of formula (II), in which X is a bond are required, these may be prepared by reacting a coumarin (V)

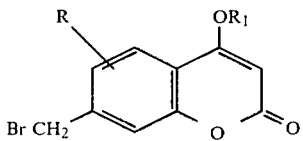

in which R and $R_1$ are as previously defined in the text with an appropriate piperazine.

As previously stated, the compounds of formula (I) are active therapeutically.

Accordingly, this invention also provides a pharmaceutical composition comprising a compound of formula (I) as defined above, or a pharmaceutically acceptable salt thereof, and a pharmaceutically acceptable carrier.

Examples of suitable and preferred compounds for inclusion in such compositions are as previously discussed.

The compositions are of course adapted for administration to human beings.

Compounds of formula (I) which are active when given by the oral route, may be compounded in the form of syrups, tablets, capsules, pills and the like. Preferably, the compositions are in unit dosage form, or in a form in which the patient can administer to himself a single dosage. When the composition is in the form of a tablet, powder or lozenge, any pharmaceutical carrier suitable for formulating solid compositions may be used. Examples of such carriers are magnesium stearate, starch, lactose, glucose, sucrose, rice flour and chalk. The composition may also be in the form of an ingestible capsule (e.g. of gelatin) containing the compound; or in the form of a syrup, a liquid solution or a suspension. Suitable liquid pharmaceutical carriers include ethyl alcohol, glycerine, saline and water which may be compounded with flavouring or colouring agents to form syrups.

The compounds of this invention may also be administered by a non-oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, antioxidants or other preservatives, buffers solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn, or as a solid form or concentrate which can be used to prepare an injectable formulation.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns. Where appropriate, small amounts of other anti-asthmatics and bronchodilators for example sympathomimetic amines such as isoprenaline, isoetharine, salbutamol, phenylephrine and ephedrine; xanthine derivatives such as theophylline and aminophylline; and corticosteriods such as prednisolone and adrenal stimulants such as ACTH may be included.

Compounds of general formula (I) may also be presented as an ointment, cream, lotion, gel, aerosol, or skin paint for topical application.

In any of the foregoing formulations, a suitable dosage unit might contain from 1 to 500 mg. of active ingredient. The effective dose of compound (I) depends on the particular compound employed, the condition of the patient and on the frequency and route of administration, but in general is in the range of from 0.01 mg/kg/day to 100 mg/kg inclusive of the patient's body weight.

As is common practice, the compositions will usually be accompanied by written or printed directions for use in the medical treatment concerned, in this case as an antiallergic agent for the prophylaxis and treatment of for example, asthma, hay-fever, rhinitis or allergic eczema.

The following Examples illustrate the preparation and properties of compounds of this invention.

EXAMPLE 1

(a) 1-Carboethoxy-4-(4-chlorobenzyl)piperazine

A mixture of 1-carboethoxypiperazine (25 g; 0.157 mole), 4-chlorobenzyl chloride (26 g; 0.162 mole) and ethanol (250 ml) was gently refluxed for 5 hours and the solvent removed in vacuo. The resulting oil crystallised on cooling to give the hydrochloride of the title compound. Recrystallisation from ethanol gave 29 g (58%) of material of m.p. 208°–210°. (Found; C, 52.70; H, 6.41; N, 8.62; Cl, 21.51; $C_{14}H_{19}ClN_2O_2$ HCl requires; C, 52.67; H, 6.31; N, 8.78; Cl, 22.20%).

Neutralisation with aqueous sodium hydroxide afforded the free base of m.p. (EtOH) 53.5°; $v_{max}$ (mull) 1700 cm$^{-1}$ (Found; C, 59.82; H, 6.81; N, 9.81; Cl, 12.19; $C_{14}H_{19}ClN_2O_2$ requires; C, 59.47; H, 6.77; N, 9.91; Cl, 12.54%).

(b) 1-(4-Chlorobenzyl)piperazine

A mixture of 1-carboethoxy-4-(4-chlorobenzyl) piperazine (3.2 g) and 2.5 N sodium hydroxide solution (100 ml) was refluxed overnight and the turbid solution clarified by addition of a minimum of ethanol. After a further 6 hours at reflux, the solution was acidified hot whereby vigorous decarboxylation ensued. The cooled mixture was basified with dilute sodium hydroxide, extracted with ether and the dried extracts evaporated to a colourless oil. Distillation gave the title compound b.p.$_{0.2}$95° in quantitative yield. (Found; C, 63.02; H, 7.36; Cl, 16.60; N, 13.41; $C_{11}H_{15}ClN_2$ requires; C, 62.70; H, 7.18; Cl, 16.83; N, 13.30%).

(c) 1-(4-Chlorobenzyl)-4-(3-chloropropyl)piperazine

A mixture of 1-(4-chlorobenzyl)piperazine (6.32 g; 0.03 mole), 1-bromo-3-chloropropane (4.75 g; 0.03 mole), anhydrous potassium carbonate (6.25 g; 0.045 mole) and butanone (75 ml) was stirred at reflux for 3 hr, cooled and filtered. The filtrate was evaporated in vacuo, and the residue dissolved in ether and washed with water (3x). The solvent solution dried over magnesium sulphate, filtered and evaporated to yield 6.86 g (80%) of the title compound. G.L.C. (5% Dexsil 300, 100°–350° at 15°/min) showed the sample to be 99% pure. A sample was distilled b.p.$_{0.5}$150°, and the distillate had the following spectral and analytical characteristics: $v_{max}$ (film) 2900, 2760, 1480, 1450, 1435 cm$^{-1}$. δ (CDCl$_3$), 1.95 (2H,m); 2.43 (10H,m); 3.42 (2H,s); 3.56 (2H,t,J 7 Hz); 7.25 (4H,s) (Found; C, 58.32; H, 7.07; Cl, 24.37; N, 9.79; $C_{14}H_{20}Cl_2N_2$ requires; C, 58.34; H, 7.02; Cl, 24.69; N, 9.75%).

(d) 1-[3-(4-Benzyloxycoumarin-7-yloxy)propyl]-4-(4-chlorobenzyl)piperazine

To a solution of 4-benzyloxy-7-hydroxycoumarin (9.4 g, 0.035 mole) in dry NN-dimethylformamide (35 ml) was added sodium hydride (0.84 g; 0.035 mole) and the mixture stirred for 1 hour at 100° to complete formation of the sodium salt. To this was added a solution of 1-(4-chlorobenzyl)-4-(3-chloropropyl)piperazine (9.3 g; 0.035 mole) in dry NN-dimethylformamide (40 ml) over 1 hour and the resulting mixture stirred for 4 hours at 100°. The precipitated sodium chloride was filtered from the cooled mixture and the filtrate evaporated in vacuo to a red oil which was extracted with dry ether. Concentration of the extracts afforded 13.5 g (74%) of white crystalline material of m.p. (EtOH) 115°–116°, $v_{max}$ (mull) 1725, 1625, 1610 cm$^{-1}$. δ (CDCl$_3$) 2.01 (2H, m); 2.48 (10H, m); 3.46 (2H, s); 4.07 (2H, t, J 6 Hz); 5.17 (2H, s); 5.65 (1H, s); 6.80 (2H, s); 7.27 (4H, s); 7.43 (5H, s); 7.72 (1H, d, J 9.6 Hz). (Found; C, 69.23; H, 6.12; Cl, 7.00; N, 5.22; $C_{30}H_{31}ClN_2O_4$ requires; C, 69.42; H, 6.02; Cl, 6.83; N, 5.40%).

(e) 1-(4-Chlorobenzyl)-4-[3-(4-hydroxycoumarin-7-yloxy)-propyl]piperazine

A solution of 1-[3-(4-benzyloxycoumarin-7-yloxy)-propyl]-4-(4-chlorobenzyl)piperazine (12 g; 0.023 mole) in dry NN-dimethylformamide (160 ml) was hydrogenated at atmospheric pressure over 10% palladinized charcoal (300 mg) until 1 equivalent of hydrogen was absorbed. The catalyst was removed by filtration and the filtrate evaporated to a white crystalline solid. Recrystallization from ethanol gave 9.45 g (96%) of material of m.p. 124°–127°, $v_{max}$ (mull) 1690, 1665, 1610 cm$^{-1}$; δ (CDCl$_3$, DMSO) 2.06 (2H, m); 2.62 (10H, m); 3.50 (2H, s); 4.04 (2H, m); 5.45 (1H broad exchangeable); 6.71 (2H, m); 7.25 (4H, s); 7.73 (1H, d, J 9.3 Hz); 8.55 (1H, broad exchangeable). (Found; C, 64.13; H, 5.92; Cl, 8.54; N, 6.32; $C_{23}H_{25}ClN_2O_4$ requires; C, 64.41; H, 5.88; Cl, 8.27; N, 6.53%).

(f) 1-(4-Chlorobenzyl)-4-[3-(4-hydroxy-3-nitrocoumarin-7-yloxy)propyl]piperazine

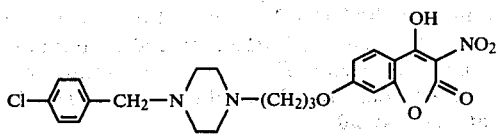

Fuming nitric acid (10 ml; d 1.52) was added dropwise over 15 mins to a cold (0° C.) stirred suspension of 1-(4-chlorobenzyl)-4-[3-(4-hydroxycoumarin-7-yloxy)-propyl]piperazine (2.0 g) in chloroform (200 ml) and the mixture stirred for a further 1 hour at 0°. The solution which formed precipitated a yellow solid on addition of water which after filtration was washed with ethanol to give 2.62; (95%) of the dinitric acid salt of the title compound of m.p. 142°–144° (dec). $v_{max}$ (mull) 2700 (br), 1740, 1615, 1525 cm$^{-1}$. (Found; C, 45.87; H. 4.52; Cl, 5.66; N, 11.36; $C_{23}H_{24}ClN_3O_6$·2HNO$_3$ requires; C, 46.05; H, 4.37; Cl, 5.91; N, 11.67%).

Neutralisation with two equivalents of aqueous sodium hydroxide gave the free base of m.p. 238°, $v_{max}$ (mull) 1695, 1605, 1565 cm$^{-1}$. (Found; C, 57.80; H, 5.24; N, 9.08; $C_{23}H_{24}ClN_3O_6$ requires; C, 58.29; H, 5.11; N, 8.87%).

The sodium salt had m.p. 220°, $v_{max}$ (mull) 3450, 1690, 1620, 1585 cm$^{-1}$. (Found; C, 54.41; H, 4.56; N, 8.58; $C_{23}H_{23}ClN_3NaO_6$·0.5H$_2$O requires; C, 54.71; H, 4.79; N, 8.32%).

EXAMPLE 2

(a) 4-Benzyloxy-7-(2,3-epoxypropyloxy)coumarin

4-Benzyloxy-7-hydroxycoumarin (10.7 g, 0.041 mole) was dissolved in ethanol (200 ml) and a solution of potassium hydroxide (2.5 g) in water (10 ml) was added.

Epichlorhydrin (40 ml) was added and the stirred mixture heated to reflux for 2½ hr. After cooling, the solvent was removed in vacuo and the residue partitioned between water and ethyl acetate. Evaporation of the dried (MgSO$_4$) organic phase gave the product as a white crystalline solid. Recrystallization from ethanol gave 11.1 g (83%) of material of m.p. 128°–129° C.; (Found; C, 70.48; H, 4.92; C$_{19}$H$_{16}$O$_5$ requires; C, 70.36; H, 4.97%).

(b)
1-[3-(4-Benzyloxycoumarin-7-yloxy)-2-hydroxypropyl]4-(4-chlorobenzyl)piperazine A mixture of 4-benzyloxy-7-(2,3-epoxypropyloxy)-coumarin (8.48 g; 0.026 mole), 1-(4-chlorobenzyl)piperazine (6.20 g; 0.0295 mole) and ethanol (50 ml) were refluxed together for 90 mins and allowed to cool. Evaporation of the solvent in vacuo gave an oily residue which crystallized on trituration with petrol ether. Recrystallization from methanol gave 8.67 g (62%) of title compound of m.p. 130°–133° C., $\nu_{max}$ (mull) 1720, 1615 cm$^{-1}$; δ (CDCl$_3$) 2.55 (10H, m); 3.20 (1H, m); 3.48 (2H, s); 4.07 (3H broad s); 5.20 (2H, s); 5.68 (1H, s); 6.89 (2H, m); 7.30 (4H, s); 7.45 (5H, s); 7.77 (1H, d, J 10 Hz). (Found: C, 67.72; H, 6.00; N, 5.29; Cl, 7.21; C$_{30}$H$_{31}$N$_2$ClO$_5$ requires; C, 67.34; H, 5.84; N, 5.24; Cl, 6.63%).

(c)
1-(4-Chlorobenzyl)-4-[2-hydroxy-3-(4-hydroxycoumarin-7-yloxy)propyl]piperazine A solution of 1-[3-(4-benzyloxycoumarin-7-yloxy)-2-hydroxypropyl]-4-(4-chlorobenzyl)piperazine (7 g) in dry DMF (80 ml) was hydrogenated at atmospheric pressure over 10% Pd/C catalyst till one equivalent of hydrogen was absorbed. Filtration and evaporation of the solvent in vacuo afforded an oily product which crystallized from ethanol/petrol to give 3.60 g (63%) of the title compound.

(d)
1-(4-Chlorobenzyl)-4-[2-hydroxy-3-(4-hydroxy-3-nitrocoumarin-7-yloxy)propyl]piperazine C$_{23}$H$_{24}$N$_3$O$_7$Cl.H$_2$O requires; C, 54.38; H, 5.16; N, 8.27; Cl, 6.98%).

EXAMPLE 3

(a)
8-Allyl-4-benzyloxy-7-(2,3-epoxypropyloxy)coumarin

Reaction of 8-allyl-4-benzyloxy-7-hydroxycoumarin (12.33 g; 0.04 mole) with epichlorhydrin (25 ml) as described in Example 2(a) gave 11.97 g (82%) of product of m.p. (ethanol) 118°–121° C., $\nu_{max}$ (mull) 1715, 1618, 1565 cm$^{-1}$ (Found; C, 72.45; H, 5.53; C$_{22}$H$_{20}$O$_5$ requires; C, 72.51; H, 5.53%).

(b)
1-[3-(8-Allyl-4-benzyloxycoumarin-7-yloxy)-2-hydroxypropyl]-4-(4-chlorobenzyl)piperazine Heating a mixture of 1-(4-chlorobenzyl)piperazine (6.2 g; 0.03 mole) and 8-allyl-4-benzyloxy-7-(2,3-epoxypropyloxy) coumarin (9.47 g; 0.026 mole) in ethanol (50 ml) to reflux for 2 hr and work-up as in Example 2(b) gave 7.85 g (52%) of the title compound of m.p. 155°–157° C., $\nu_{max}$ (mull) 3320, 1675, 1615, 1605, 1565 cm$^{-1}$; (Found; C, 69.04; H, 6.20; N, 4.67; Cl, 6.12; C$_{33}$H$_{35}$O$_5$N$_2$Cl requires; C, 68.92; H, 6.13; N, 4.87; Cl, 6.17%).

(c)
1-(4-Chlorobenzyl)-4-[2-hydroxy-3-(4-hydroxy-8-n-propylcoumarin-7-yloxy)propyl]piperazine Hydrogenation of a solution of 1-[3-(8-allyl-4-benzyloxycoumarin-7-yloxy)-2-hydroxypropyl]-4-(4-chlorobenzyl)piperazine (7.2 g) in DMF (200 ml) over 10% palladinized charcoal at atmospheric pressure until two equivalents of hydrogen were absorbed gave 4.85 g (80%) of material of m.p. (aqueous ethanol) 107° C. (Found; C, 63.90; H, 6.59; N, 5.20; Cl, 6.53; C$_{26}$H$_{31}$N$_2$O$_5$Cl requires; C, 64.12; H, 6.42; N, 5.75; Cl, 7.28%).

(d)
1-(4-Chlorobenzyl)-4-[2-hydroxy-3-(4-hydroxy-3-nitro-8-n-propylcoumarin-7-yloxy)propyl]piperazine

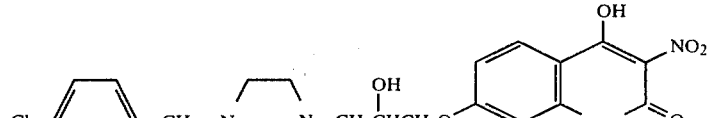

To a stirred solution of 1-(4-chlorobenzyl)-4-[2-hydroxy-3-(4-hydroxy-8-n-propylcoumarin-7-yloxy)propyl]piperazine (3 g) in chloroform (200 ml) was added fuming nitric acid (9 ml) over 1 hr at room temperature. After stirring for a further 1 hr the mixture was stripped of solvent in vacuo and water added. The precipitated dinitric acid salt was filtered off and dried Fuming nitric acid (7.5 ml; d 1.52) was added dropwise over 1 hr to a stirred suspension of 1-(4-chlorobenzyl)-4-[2-hydroxy-3-(4-hydroxycoumarin-7-yloxy)-propyl]piperazine (2.60 g) in chloroform (250 ml) over 1 hr at room temperature and the mixture stirred for a further 1 hr. Work-up afforded 2.88 g (80%) of dinitric acid salt which was converted to the free base of m.p. 185° C., (Found; C, 54.33; H, 4.89; N, 7.93; Cl, 6.97;

to give 3.60 g (89%) of material of m.p. 126°–127° C. (dec.); (Found: C, 47.46; H, 4.95; N, 9.27; Cl, 5.18; $C_{26}H_{30}N_3O_7Cl.2HNO_3$ requires; C, 47.45; H, 4.90; N, 10.65; Cl, 5.39%).

The free base, formed from the above salt by dissolution in aqueous sodium hydroxide solution and reacidification with acetic acid, had m.p. 96°–97° C.; (Found; C, 56.53; H, 6.01; N, 7.48; Cl, 6.57; $C_{26}H_{30}N_3O_7Cl.H_2O$ requires; C, 56.77; H, 5.86; N, 7.64; Cl, 6.44%).

EXAMPLE 4

(a) 1-(4-Chlorobenzyl)-4-(2-chloroethyl)piperazine

A mixture of 1-(4-chlorobenzyl)piperazine (21.05 g; 0.1 mole), anhydrous potassium carbonate (20.7 g; 0.15 mole) and 2-chloroethanol (8.85 g; 0.11 mole) in butanone (270 ml) was stirred at reflux for 6½ hr, cooled, and the solvent removed in vacuo. Chromatography of the residue on silica eluting with chloroform gave 8.74 g (34%) of the title compound as an oil, $\nu_{max}$ (film) 3350, 2910, 2800, 1595 cm$^{-1}$; (Found; C, 61.48; H, 7.96; N, 10.13; $C_{13}H_{19}N_2ClO$ requires; C, 61.28; H, 7.52; N, 11.00%).

(b) 1-(4-Chlorobenzyl)-4-[2-(4-ethoxycoumarin-7-yloxy)ethyl]piperazine

A suspension of 4-ethoxy-7-hydroxycoumarin (6.47 g) in dry tetrahydrofuran (THF, 1 liter) and triphenylphosphine (9.07 g) were stirred at room temperature while diethylazodicarboxylate (6.02 g) in THF (25 ml) was added portionwise over 5 mins. To this mixture was added 1-(4-chlorobenzyl)-4-(2-chloroethyl)piperazine (8 g) in THF (100 ml) over 15 mins and the total stirred at room temperature for 30 mins. Evaporation of the solvent in vacuo (<25° C.) gave an oil which was dissolved in a minimum of ethanol and the dihydrochloride salt of the product precipitated by the addition of concentrated hydrochloric acid. Filtration and drying gave 9.30 g (58%) of dihydrochloride of m.p. 245°–247° C.; (Found; C, 54.69; H, 5.55; N, 5.53; $C_{24}H_{27}N_2O_4Cl.2HCl$ requires; C, 55.87; H, 5.67; N, 5.43%).

(c) 1-(4-Chlorobenzyl)-4-[2-(4-hydroxycoumarin-7-yloxy)ethyl]piperazine

A mixture of 1-(4-chlorobenzyl)-4-[2-(4-ethoxycoumarin-7-yloxy)ethyl]piperazine (9 g), glacial acetic acid (200 ml) and concentrated hydrochloric acid (50 ml) was refluxed for 30 mins, cooled, and the solution evaporated to dryness. The residual solid was suspended in ethanol, filtered off and dried to give 6.22 g (73%) of the dihydrochloride of the title compound of m.p. 275°–278° C. (dec).

(d) 1-(4-Chlorobenzyl)-4-[2-(4-hydroxy-3-nitrocoumarin-7-yloxy)ethyl]piperazine

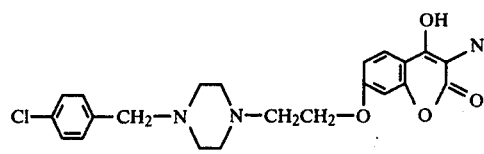

Fuming nitric acid (15 ml) was added over 1 hr to a stirred suspension of 1-(4-chlorobenzyl)-4-[2-(4-hydroxycoumarin-7-yloxy)ethyl]piperazine (5 g) in chloroform (500 ml) at room temperature and after a further 10 mins the reaction mixture was diluted with water (200 ml). Removal of the chloroform in vacuo gave a yellow solid which was filtered off, washed with water and dried to give 4.66 g of dinitric acid salt of m.p. 207°–209° C. (dec). Conversion to the free base afforded material of m.p. 171° C.; (Found; C. 53.51; H, 4.69; N, 8.18; $C_{22}H_{22}N_3Cl.2H_2O$ requires; C, 53.27; H, 5.28; Cl, 8.47%).

EXAMPLE 5

(a) 4-Ethoxy-7-methylcoumarin

Dry hydrogen chloride was passed through a solution of 4-hydroxy-7-methylcoumarin (14 g; 0.08 mole) in ethanol (300 ml) for 15 mins and the resulting solution was refluxed for 30 minutes. After cooling, the solvent was removed in vacuo and the residue recrystallized from ethanol to give 11.74 g (72%) of product of m.p. 142°–143° C.; (Found; C, 70.24; H, 5.95; $C_{12}H_{12}O_3$ requires; C, 70.60; H, 5.88%).

(b) 7-Bromomethyl-4-ethoxycoumarin

N-Bromosuccinimide (9.59 g; 0.054 mole) was added to stirred solution of 4-ethoxy-7-methylcoumarin (11 g; 0.054 mole) in carbontetrachloride (600 ml) followed by a catalytic quantity of azo bisbutyronitrile. After refluxing the mixture for 1 hr the solvent was removed in vacuo and the residue recrystallized from ethanol to give 11.73 g (77%) of product of m.p. 150°–3° C. Further recrystallization gave material of m.p. 152°–155° C.

(c) 1-(4-Chlorobenzyl)-4-[(4-ethoxycoumarin-7-yl)methyl]piperazine

A mixture of 1-(4-chlorobenzyl)piperazine (4.21 g), 7-bromomethyl-4-ethoxycoumarin (5.80 g) and anhydrous potassium carbonate (4.2 g) in chlorobenzene (50 ml) were stirred for 20 hr at 140° C. and the cooled solution treated with dilute hydrochloric acid. The precipitated solid was filtered off, washed well with water and dried to give 5.00 g (50%) of dihydrochloride of m.p. 260°–264° C. The free base had m.p. 122°–124° C.

(d) 1-(4-Chlorobenzyl)-4-[(4-hydroxycoumarin-7-yl)methyl]piperazine

Hydrolysis of 1-(4-chlorobenzyl)-4-[(4-ethoxycoumarin-7-yl)methyl]piperazine (1.5 g) as described in Example 4(c) gave the hydroxy compound as its dihydrochloride in quantitative yield, m.p. 277° C.; (Found; C, 55.08; H, 5.16; N, 5.97; Cl, 23.13; $C_{21}H_{21}N_2O_3Cl.2HCl$ requires; C, 55.09; H, 5.06; N, 6.12; Cl, 23.24%).

(e) 1-(4-Chlorobenzyl)-4-[(4-hydroxy-3-nitrocoumarin-7-yl)methyl]piperazine

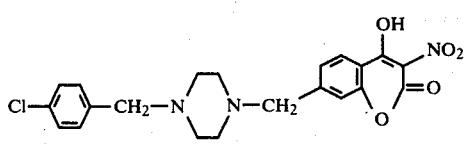

Nitration of 1-(4-chlorobenzyl)-4-[(4-hydroxycoumarin-7-yl-methyl]piperazine (1.0 g) as described in Example 4(d) afforded 1.0 g of the dinitric acid salt of the title compound of m.p. 134° C.; (Found; C, 43.52; H, 4.12; N, 11.71; Cl, 6.92; $C_{21}H_{20}N_3O_5Cl.2HNO_3.H_2O$ requires: C, 43.94; H, 4.21; N, 12.20; Cl, 6.38%).

Conversion to the free base as previously described gave compound of m.p. 239°–240° C.; (Found; C, 56.29; H, 4.90: N, 9.19: Cl, 8.24; $C_{21}H_{20}N_3O_5Cl.H_2O$ requires; C, 56.32; H, 4.95; N, 9.38; Cl, 7.92%).

EXAMPLE 6

(a) 1-Benzyl-4-(3-hydroxypropyl)piperazine

Alkylation of 1-benzylpiperazine (16 g, 0.091 mole) with 3-bromopropan-1-ol (13.88 g; 0.01 mole) as described in Example 1(c) gave, after chromatography, 12.9 g (61%) of the product as a colourless oil. $\nu_{max}$ (film) 3300, 2920, 2800, 1595 cm$^{-1}$; (Found; C, 69.41; H, 9.60; N, 11.75; $C_{14}H_{22}N_2O.0.5H_2O$ requires; C, 69.10; H, 9.52; N, 11.51%).

(b) 1-Benzyl-4-[3-(4-ethoxycoumarin-7-yloxy)propyl]piperazine

Condensation of 1-benzyl-4-(3-hydroxypropyl)piperazine (12.5 g) with 4-ethoxy-7-hydroxycoumarin (11 g) as described in Example 4(b) gave 13.8 g (52%) of the title compound as its dihydrochloride of m.p. (ethanol) 240°–241° C.; (Found; C, 59.89; H, 6.47; N, 5.68; Cl, 14.44; $C_{25}H_{30}N_2O_4.2HCl$ requires; C, 60.60; H, 6.51; N, 5.66; Cl, 14.31%).

(c) 1-Benzyl-4-[3-(4-hydroxycoumarin-7-yloxy)propyl]piperazine

Hydrolysis of 1-benzyl-4-[3-(4-hydroxycoumarin-7-yloxy)propyl]piperazine (13.8 g) with hydrochloric acid in acetic acid as described in Example 4(c) gave 10.42 g (80%) of the dihydrochloride of the title compound of m.p. 215°–218° C. (dec).

(d) 1-Benzyl-4-[3-(4-hydroxy-3-nitrocoumarin-7-yloxy)-propyl]piperazine

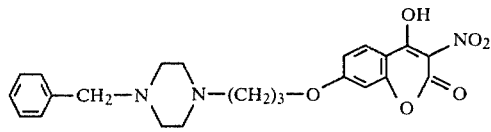

Nitration of 1-benzyl-4-[3-(4-hydroxycoumarin-7-yloxy)propyl]piperazine (6.08 g) as described in Example 4(d) gave 6.42 g of the 3-nitro-derivative as its dinitric acid salt of m.p. 128°–129° C. Conversion to the free base gave material of m.p. 227° C.; (Found; C, 62.40; H, 5.86; N, 9.63; $C_{23}H_{23}N_3O_6$ requires; C, 62.85; H, 5.72; N, 9.56%).

PHARMACOLOGICAL DATA SECTION

Activities in biological test systems

The compounds were tested for their ability to:
(a) inhibit rat passive peritoneal anaphylaxis; and
(b) antagonise the spasmogenic effects of histamine on isolated guinea pig ileum.

The methods used are described below.

(a) Rat passive peritoneal anaphylaxis (PPA)

The method has been described previously (Ross, Janet W., Smith, H. and Spicer, Barbara A. Increased vascular permeability during passive peritoneal anaphylaxis in the rat. Int. Arch. Allergy appl. Immun. 51, 226, 1976.)

Antiserum

Serum containing heat-labile homocytotropic antibody was raised in rats to ovalbumin by a method similar to that described by Mota, I. (The mechanism of anaphylaxis. I. Production and biological properties of mast cell sensitising antibody. Immunology, 7, 681; 1964). Male Wistar rats of 250–300 g were given intraperitoneal injections of 0.5 ml of Bordetella pertussis vaccine ($4 \times 10^{10}$ organisms/ml; Burroughs Wellcome, London) and subcutaneous injections of 0.5 ml of an emulsion of 100 mg of ovalbumin in 2 ml of isotonic saline and 3 ml of Freund's incomplete adjuvant. The rats were bled by cardiac puncture on day 18, the blood was pooled and the serum separated, stored at $-20°$ C. and thawed only once before use. The serum produced PCA activity in recipient rats down to a dilution of 1:32 to 1:64 after 72 hr and persisted for several days. This activity was lost to a dilution of 1:2 by heating at 56° for 4 hr even when the sensitising period was reduced to 4 hr.

Passive peritoneal anaphylaxis

Rats were given intraperitoneal injections of 2 ml of a 1:5 dilution of the rat anti-serum in isotonic saline. 2 hr later 0.3 ml of a 5% solution of Pontamine Sky Blue (Raymond A. Lamb, London) is isotonic saline was injected intravenously, followed by an intraperitoneal injection of the test compound in 1 ml of saline; (control rats received 1 ml of saline); followed 30 sec. later by an intraperitoneal injection of 5 ml of a Tyrode solution containing 50 μg/ml heparin and 0.4 mg/ml of ovalbumin. The concentrations of the compounds were quoted as those in the 6 ml of fluid injected intraperitoneally. Extractly 5 min. after challenge the rats were stunned and bled and their peritoneal fluids were collected by opening their peritoneal cavities over funnels into polycarbonate tubes in ice. The supernatants were separated from the cellular residue by centrifuging at 150 g for 5 min. and any samples obviously contaminated with blood were discarded and the remainder were retained for estimation of dye, histamine and SRS-A. Groups of at least 5 rats were used for each dose of compound and the treatments were randomized.

Assay of peritoneal fluids

Collected peritoneal fluids were immediately cooled to 0° C. and centrifuged and the supernatant fluids assayed for dye within 2 hr. 0.5-ml samples of the supernatants were added to 1 ml of 12% trichloracetic acid and stored at $-20°$ C. and used to assay for histamine. The remainders of the supernatant fluids were placed in a boiling water bath for 5 min. and stored frozen at $-20°$ C. until assayed for SRS-A.

Dye Assay

The optical densities (OD) at 625 nm of the supernatants were determined. Samples were taken from supernatants with an OD greater than 2 and diluted in Tyrode's solution before reading.

Histamine Assay

Histamine was assayed using an automated spectrofluorimetric system (Technicon Autoanalyser) by a method similar to that of Evans, D. P., Lewis, J. A. and Thomson, D. S.: (An automated fluorimetric assay for the rapid determination of histamine in biological fluids. Life Sci. 12, 327, 1973). At the concentrations used the compounds tested did not interfere with the assay.

SRS-A Assay

SRS-A was assayed on the isolated guinea pig ileum preparation in the presence of atropine ($5\times10^{-7}$ M) and mepyramine maleate ($10^{-6}$ M), the latter to abolish the histamine response. (Brocklehurst, W. E. The release of histamine and formulation of a slow reacting substance (SRS-A) during anaphylactic shock. J. Physiol., Lond. 151, 416, 1960). Bulked peritoneal fluids from passively sensitised and challenged rats were centrifuged, heated, stored at $-20°$ C. in 0.5 ml aliquots, and used as a reference SRS-A standard, and arbitrarily designated as containing 10 Units per ml. Concentrations of the unknown were bracketed by reference SRS-A samples. At the concentrations used, the compounds tested did not interfere with the assay.

(b) Measurement of anti-histamine activity in vitro on guinea pig ileum using the pH$_2$ scale The pA$_2$ of the compound was determined in a similar manner to that described by Schild, H. O. (pA, A new scale for the measurement of drug antagonism. Brit. J. Pharmacol. 2, 189, 1947).

Results

The results obtained in these tests, which are shown in the following Table, demonstrate the ability of the compounds not only to inhibit the release of mediator substances but also to antagonize the effects of released histamine.

TABLE

| Compound of Example No. | Conc. Injected I.P. (M) | Concentrations in Peritoneal Fluid as % of that in control rats not given compound Mean ± SEM, 3-7 rats per group | | |
|---|---|---|---|---|
| | | Histamine | SRSA | DYe |
| 1f | $2\times10^{-8}$ | 99.6 ± 8.3 | 100 ± 14.8 | 100 ± 16.7 |
| | $2\times10^{-7}$ | 75.8 ± 7.5 | 71.8 ± 14.8 | 88.1 ± 8.3 |
| | $2\times10^{-6}$ | 28.4 ± 3.4 | 62.5 ± 17.2 | 32.1 ± 3.6 |
| 2d | $2\times10^{-6}$ | 23 ± 1.0 | 65 ± 13 | 46 ± 4 |
| | $2\times10^{-5}$ | 13 ± 0.9 | 47 ± 11 | 36 ± 4 |
| 3d | $2\times10^{-6}$ | 55 ± 9 | 81 ± 6 | 79 ± 9 |
| | $2\times10^{-5}$ | 15 ± 2 | 75 ± 9 | 47 ± 6 |
| 4d | $2\times10^{-5}$ | 39 ± 8 | 73 ± 7 | 65 ± 11 |
| | $2\times10^{-4}$ | 11 ± 0.9 | 26 ± 6 | 40 ± 7 |
| | $2\times10^{-6}$ | 93 ± 18 | 94 ± 10 | 103 ± 13 |
| 5e | $2\times10^{-5}$ | 31 ± 2 | 67 ± 15 | 88 ± 14 |
| | $2\times10^{-4}$ | 17 ± 3 | * | 28 ± 9 |
| 6d | $2\times10^{-5}$ | 56 ± 8 | 86 ± 14 | 91 ± 12 |
| | $2\times10^{-4}$ | 12 ± 1.0 | 55 ± 5 | 67 ± 10 |

*Compound interefered with bioassy

| Compound of Example No. | Antihistamine Activity (in vitro) | | |
|---|---|---|---|
| | Contact Time (mins) | pA$_2$ Mean ± SEM | No. of guinea pig ilea |
| 1f | 0.5 | 7.8 | 1 |
| | 2.0 | 8.6 ± 0.1 | 4 |
| | 10.0 | 9.2 ± 0.1 | 4 |
| 2d | 0.5 | 7.3 | 1 |
| | 2.0 | 7.7 | 2 |
| | 10.0 | 8.3 | 2 |
| 3d | 0.5 | 7.6 | 2 |
| | 2.0 | 8.0 | 1 |
| | 10.0 | 8.4 | 2 |
| 4d | 0.5 | 7.2 ± 0.06 | 4 |
| | 2.0 | 7.3 | 2 |
| | 10.0 | (~6.9) | (part assay) |
| 5e | 0.5 | 5.7 | 2 |
| | 2.0 | 5.7 | 1 |
| | 10.0 | 5.6 | 1 |
| 6d | 0.5 | 7.1 | 1 |
| | 2.0 | 7.6 | 2 |
| | 10.0 | 7.9 | 1 |

N.B. Dosages of Compounds as for other test

Toxicity

1. No toxic effects were observed in these tests.
2. Detailed toxicological data was obtained for the compound of Example 1(f), as follows:

No deaths occurred during four days in three groups of ten mice given doses of 1, 3 and 10 mg/kg of the compound of Example 1(f) intravenously.

In three groups of three mice given 30, 90 and 300 mg/kg of the compound of Example 1(f) intravenously all animals died at the high dose but none at the two lower doses. The intravenous LD$_{50}$ in mice therefore lies between 100-300 mg/kg.

What we claim is:

1. A compound of the formula (I):

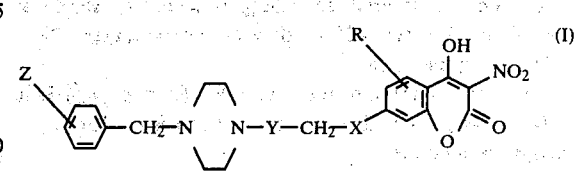

and pharmaceutically acceptable salts thereof, wherein R is hydrogen or an alkyl group containing up to 6 carbon atoms; X is a bond or oxygen; Y is —(CH$_2$)$_n$— where n is 0 or an integer from 1 to 5 wherein one carbon atom not bound to the nitrogen atom may be optionally substituted with a hydroxy group; and Z is hydrogen or halogen.

2. A compound according to claim 1, wherein Z is hydrogen, chlorine or bromine.

3. A compound according to claim 2, wherein Z is in the p-position in its phenyl ring with respect to the —CH$_2$— substituent.

4. A compound according to claim 3, wherein Z is chlorine.

5. A compound according to claim 1, wherein Y is alkylene.

6. A compound according to claim 5, wherein Y is methylene, ethylene or propylene.

7. A compound according to claim 6, wherein Y is ethylene.

8. A compound according to claim 1, wherein the compound of formula (I) is of formula (I)':

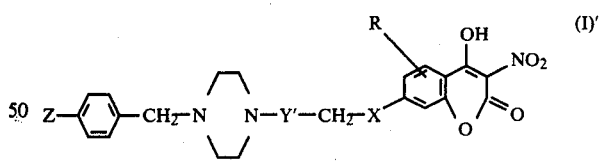

wherein R, X and Z are as defined in formula (I), and Y' is —(CH$_2$)$_n$— where n is 0 or an integer from 1 to 5.

9. A compound according to claim 8, wherein Z is chlorine.

10. A compound according to claim 8, wherein Y' is ethylene.

11. An anti-allergenic pharmaceutical composition comprising a compound according to claim 1, and a pharmaceutically acceptable carrier.

12. A method of prophylaxis or treatment of allergic diseases, which method comprises the administration of an amount effective to inhibit the release of the mediators of the allergic response and to antagonize the effects of released histamine of a compound according to claim 1.

13. The compound according to claim 1, which is 1-(4-Chlorobenzyl)-4-[3-(4-hydroxy-3-nitrocoumarin-7-yloxy)propyl]piperazine.

14. The compound according to claim 1, which is 1-(4-Chlorobenzyl)-4-[2-hydroxy-3-(4-hydroxy-3-nitrocoumarin-7-yloxy)propyl]piperazine.

15. The compound according to claim 1, which is 1-(4-Chlorobenzyl)-4-[2-hydroxy-3-(4-hydroxy-3-nitro-8-n-propylcoumarin-7-yloxy)propyl]piperazine.

16. The compound according to claim 1, which is 1-(4-Chlorobenzyl)-4-[2-(4-hydroxy-3-nitrocoumarin-7-yloxy)ethyl]piperazine.

17. The compound according to claim 1, which is 1-(4-Chlorobenzyl)-4-[(4-hydroxy-3-nitrocoumarin-7-yl)methyl]piperazine.

18. The compound according to claim 1, which is 1-Benzyl-4-[3-(4-hydroxy-3-nitrocoumarin-7-yloxy)propyl]piperazine.

19. The composition according to claim 11, wherein the compound is 1-(4-Chlorobenzyl)-4-[3-(4-hydroxy-3-nitrocoumarin-7-yloxy)propyl]piperazine.

20. The composition according to claim 11, wherein the compound is 1-(4-Chlorobenzyl)-4-[2-hydroxy-3-(4-hydroxy-3-nitrocoumarin-7-yloxy)propyl]piperazine.

21. The composition according to claim 11, wherein the compound is 1-(4-Chlorobenzyl)-4-[2-hydroxy-3-(4-hydroxy-3-nitro-8-n-propylcoumarin-7-yloxy)propyl]piperazine.

22. The composition according to claim 11, wherein the compound is 1-(4-Chlorobenzyl)-4-[2-(4-hydroxy-3-nitrocoumarin-7-yloxy)ethyl]piperazine.

23. The composition according to claim 11, wherein the compound is 1-(4-Chlorobenzyl)-4-[(4-hydroxy-3-nitrocoumarin-7-yl)methyl]piperazine.

24. The composition according to claim 11, wherein the compound is 1-Benzyl-4-[3-(4-hydroxy-3-nitrocoumarin-7-yloxy)propyl]piperazine.

* * * * *